(12) United States Patent
Khanuja et al.

(10) Patent No.: US 6,423,541 B1
(45) Date of Patent: Jul. 23, 2002

(54) PROCESS FOR IN VITRO SELECTION OF HIGH METHOL PRODUCING GENOTYPES

(75) Inventors: Suman Preet Singh Khanuja; Ajit Kumar Shasany; Sunita Dhawan; Mahendra Pandurang Darokar; Tiruppadiripuliyur Ranganathan Santha Kumar; Dharmendra Saikia; Arif Ali Naqui; Sushil Kumar, all of Lucknow (IN)

(73) Assignee: Council of Scientific&Industrial Reaearch, New Delhi (IN)

( * ) Notice: Subject to any disclaimer, the term of this patent is extended or adjusted under 35 U.S.C. 154(b) by 0 days.

(21) Appl. No.: 09/531,768

(22) Filed: Mar. 21, 2000

(51) Int. Cl.[7] .................................................. C12N 5/00
(52) U.S. Cl. ........................ 435/420; 435/410; 435/421; 435/430; 435/430.1; 435/431
(58) Field of Search ................................. 435/410, 420, 435/421, 430, 430.1, 431

(56) References Cited

U.S. PATENT DOCUMENTS 5,898,001 A * 4/1999 Kumar et al. ................ 435/430

* cited by examiner

Primary Examiner—Leon B. Lankford, Jr.
(74) Attorney, Agent, or Firm—Nath & Associates PLLC; Harold L. Novick (57) ABSTRACT

The invention provides a rapid in vitro method for selection of menthol rich mint genotypes from a large population of independent clones, said method comprising the steps of (i) raising a heterogeneous population of *Mentha arvensis* clones in vitro or by vegetative methods, (ii) transferring the plantlets/shoots to a basal medium, containing cytotoxic compounds in an amount sufficient to cause toxic effect in more than 95% of the clones, (iii) selecting surviving clones, their hardening in the glasshouse, transfer to field, reconfirmation of menthol tolerance through repeated in vitro assays, and (iv) multiplying selected clones and confirming genetic uniformity through RAPD analysis.

8 Claims, 5 Drawing Sheets

(3 of 5 Drawing Sheet(s) Filed in Color)

PROCESS FOR IN VITRO SELECTION OF HIGH METHOL PRODUCING GENOTYPES

FIELD OF THE INVENTION

The present invention relates to an in vitro selection procedure used to select high menthol producing genotypes from in vitro raised somaclonal variants or among vegetatively propagated large population of *Mentha arvensis* clones.

BACKGROUND OF THE INVENTION

The industrial mint crops have found wide cultivation in several countries for the commercial production of essential oils due to the economic importance of the monoterpene components. The essential oil of *Mentha arvensis* Linn. var Piperascens is a well known source of the monoterpene 'menthol' used in the cosmetics, pharmaceutical, food, confectionery and liquor industries. The biosynthesis of menthol in the plant is regulated in a coordinated cascade fashion during plant differentiation. Specific oil glands (trichomes) formed on the surface of the leaf isolate these toxic monoterpenoid products to prevent the cellular damage. Various methods of breeding using intra and inter-specific hybridisations, clonal selections induced mutagenesis are being attempted for genetic improvement of this plant. But the main impediment is gyanodioecy and polyploid nature which results in the male sterile hybrids which hamper further screening of high menthol strains. Similarly, improvement of the genotypes by somaclonal variations requires the screening of a large number of clones for menthol content. Monoterpenes are cytotoxic to plant tissues and act through inhibition of respiration and photosynthesis by drastically affecting the mitochondria, golgi bodies etc. and decreasing cell membrane permeability. In the present invention for the exploratory experimentation the applicants compared the menthol content in the oil of selected cultivars of *Mentha arvensis* Linn. var Piperascens released by CIMAP.

These varieties were also checked for the in vitro menthol tolerance level by the regenerated shoots from these genotypes by inoculating on menthol containing medium. The main objective here was to explore the possible relationship between these two characters. Keeping in view the rationale of feed back toxicity by metabolic end product (menthol), the correlation could be utilized as a probing and selective tool to identify high menthol clones.

The applicants have earlier reported a high efficiency protocol for rapid generation, detection and selection of somaclonal variants through molecular approach in *Mentha arvensis* (S P S Khanuja, A K Shasany, S Dhawan, S Kumar, 1998, Rapid procedure for isolating somaclones of altered genotypes in *Mentha arvensis*. Journal of Medicinal and Aromamatic Plants Science, 20: 359–361). The applicants have also successfully defined the conditions and media for stable micropropagation of selected clones (A K Shasany, S P S Khanuja, S Dhawan, U Yadav, S Sharma, S Kumar, 1998, High regenerative nature of *Mentha arvensis* internodes. Journal of Biosciences 23: 641–646).

In the present invention, the applicants utilized the former protocol (Khanuja el at., 1998) to generate and capture the somaclonal variants at molecular level in larger frequencies. The applicants then screened the somaclones for their levels of in vitro tolerance to menthol in poison agar medium by devising a novel method for rapid and dependable selection of tolerant clone(s) right at the tissue culture stage. Further the tolerant plants, which survived were multiplied by the latter protocol (Shasany et al, 1998) and tested for their stability, essential oil, menthol content and biomass yield upto field level

Objects

The main object of the invention is to develop an in vitro method for selection of high menthol producing genotypes from somaclonal variants or vegetatively propagated large population of *Mentha arvensis* clones.

Another object is to provide a method or a table for the identification or selection of menthol-rich genotypes from a large population of *Mentha arvensis* clones.

SUMMARY

Accordingly, the invention provides a method for the selection of menthol rich or high menthol producing genotypes from a large population of *Mentha arvensis* clones.

DETAILED DESCRIPTION

Accordingly, tee invention provides a new, simple and rapid in vitro method for selection of menthol rich mint genotypes from a large population of independent clones, comprising the steps of:

(i) raising a heterogeneous population of *Mentha arvensis* clones in vitro or by vegetative methods, (ii) transferring the plantlets/shoots to a basal medium containing selective compounds in an amount sufficient to cause toxic effect in more than 95% of time clones, (iii) selecting surviving clones, their hardening in the glasshouse, transfer to field, reconfirmation of menthol tolerance through repeated in vitro assays, and (iv) multiplying selected clones and confirming genetic uniformity through RAPD analysis before menthol yield field trial.

In an embodiment, the vegetative methods for raising a heterogeneous population of *Mentha arvensis* clones in vitro comprise development of suckers/runners, open pollinated seed progeny, plants raised from seeds produced by planned hybridization between selected parents through controlled pollination.

In still another embodiment, the basal medium comprises MS medium containing cytotoxic compounds in a concentration sufficient to cause irreversible wilting, browning, or death of more than 95% of the plants.

In a further embodiment, the compounds for selection are selected from menthol, monoterpenes and such similar compounds. In one embodiment, the most preferred cytotoxic compounds are menthol and monoterpenes.

In another embodiment, the menthol rich mint genotypes yield at least 74% or more menthol in their essential oils.

In yet another embodiment, the screening result can also be used as the rapid indicator of menthol yield different varieties for evaluation purpose.

In yet another embodiment, the selection pressure is the concentration of menthol (50 and 80 $\mu$g ml$^{-1}$), which causes the lethality of at least 95% of clones/plantlets and the selection pressure is not limited to menthol as other monoterpenes and cytotoxic compounds can also be used.

In the other embodiment, the compounds for selection are toxic to cytoplasm causing complete loss of chlorophyll in the lower leaves and gradually covering the whole shoot within a week time leading to death of the shoot.

In another embodiment, the compounds for selection are selected from the group comprising nerol, geraniol, citronellol linalool, myrcene, terpineol limolene, cineole, terpinol, terpinene, cymene, thymol, carvone, pinene, fenchol, fenchone, camphene, borneol, camphor, thujone, thujanol, sabinene, carene and other related compounds.

In the other embodiment, the procedure can be carried out in any suitable agar medium with selective compound in sterilizable flasks, tubes or containers of various sizes permitting the proper growth conditions to the shoots/plantlets.

The file of this patent contains at least one drawing executed in color. Copies of this patent with color drawing(s) are provided to the Patent and Trademark Office with payment of the necessary fee.

The invention is described in detail hereafter with reference to the accompanying drawings, wherein.

Lane 1 Molecular weight marker ($\lambda$ Hind III+Eco RI)
Lane 2: Clone no 3; Lane 3: Clone no 14, Lane 4: Clone no 24; Lane 5: Clone no 27; Lane 6: Clone no 30; Lane 7: Control cv. Himalaya.

Lane 1: Molecular weight marker ($\lambda$ Hind III+Eco RI);
Lane 2: Clone no 3; Lane 3: Clone no 14, Lane 4: Clone no 24; Lane 5: Clone no 27; Lane 6: Clone no 30; Lane 7: Control cv. Himalaya following examples have been provided merely to illustrate the invention and should not be construed to limit the scope of the invention in any manner.

EXAMPLES (A) Establishing the relationship of menthol tolerance to menthol content in genetically different mint varieties The plant varieties analysed were Himalaya, Shivalik, Gomti, MAS-1, Kosi, Kalka of *Mentha arvensis* L. (2n=96). The suckers of these plant varieties were obtained from CIMAP's national gene bank for medicinal and aromatic plants for planting. The explant materials were collected from the field grown plants and surface sterilized by washing sequentially with 2% detergent, distilled water containing a few drops of Savlon (Johnson and Johnson, India), 0.1% acidified mercuric chloride and autoclaved distilled water before inoculation. About 1 cm long internodal pieces were inoculated in the MS medium (Murasighe and Skoog, 1962) containing vitamins, 100 mg l$^{-1}$ myo-inositol 3% wv$^{-1}$ sucrose, 1.5% wv$^{-1}$ agar (Difco), 0.5 $\mu g$ ml$^{-1}$ of an auxin, (NAA, 1-napthalene acetic acid) and 5 $\mu g$ ml$^{-1}$ of a cytokinin (BAP, benzyl aminopurine) (Shasany et al, 1998). The cultures were grown at 25±2° C. and 400 to 600 lux light intensity with 16 h photoperiod. The regenerated shoots were separated 12 weeks after the explant inoculation for rooting and/or testing menthol tolerance.

The regenerated shoots (3–4 cm long, containing the apical bud and 2–3 nodes) separated after 12 weeks, were inoculated into MS basal medium with or without menthol (0 to 100 $\mu g$ ml$^{-1}$). Concentration of menthol in each treatment was stepped up by 10 $\mu g$ in a sequential manner. On each kind of these media, 5 independently regenerated shoots were inoculated per flask; 4 flasks were inoculated per replication and each treatment was replicated 5 times, making the number of flasks to 20 and number of explants to 100 for each concentration of menthol. The experiment was conducted in the completely randomized design (CRD) fashion. Cultures were incubated and maintained at 25±2° C. and 400–600 lux light intensity with 16-hour photoperiod. The wilting response and lethality in explants was recorded every 24 hours over a period of one week.

With the increase in menthol concentration in the medium, the survival of the regenerated shoots showed corresponding decrease (Table 1). Similar inverse relationship trends were observed when these cultures were incubated for 24 h to 7 days. The dying shoots did not revive even upon changing the growth hormones and withdrawing menthol from the media. Twenty-four hours after incubation 100%, 98%, 99%, 98%, 99% and 98% lethality was observed for the cultivars Himalaya, Shivalik, Gomti, MAS-1, Kosi and Kalka respectively at 100-ppm menthol concentration. Effect on survival rate of the shoots was detected in all treatments of more than 40-ppm menthol level in the medium. But at inter-varietal level the survival frequency was invariably higher for MAS-1 and Kalka at all the higher menthol concentrations (>40 ppm) in comparison to the other cultivars Similarly, after 7 days of incubation at 40-ppm and above concentration of menthol, shoot lethality was observed for all the cultivars. At 80 ppm menthol concentration, 100% mortality of shoots was observed for all varieties except in case of MAS-1 which showed 2% survival. MAS-1 and Kalka cultivars showed higher tolerance level compared to all other varieties even after 7 days of incubation.

Oil samples from the fresh leaves of all the cultivars grown in the CIMAP Farm were extracted by hydrodistillation using Clevenger's apparatus. GLC analysis was performed using a Varian Vistas 6000 Gas Chromatogram with 6'×⅛" stainless steel column packed with 10% carbowax 20M+TPA on chromosorb W(AW) 80/100 mesh, fitted with a flame ionisation detector. Interestingly, although lowest essential oil content was observed for MAS-1 (0.50%) followed by Kalka (0.57%) the menthol yield was highest for MAS-1 followed by Kalka compared to all other cultivars taken in this study (Table 2).

TABLE 1

Survival of in vitro raised shoots of mint varieties at different concentrations of menthol.

| Concentration of menthol | Number of shoots tested per | Survival after 24 hours Number | | | | | |
|---|---|---|---|---|---|---|---|
| mg ml$^{-3}$ | replication | Himalaya | Shivalik | Gomti | MAS-1 | Kosi | Kalka |
| 0 | 20 | 20.0 ± 0.00 | 20.0 ± 0.00 | 20.0 ± 0.00 | 20.0 ± 0.00 | 20.0 ± 0.00 | 20.0 ± 0.00 |
| 10 | 20 | 20.0 ± 0.00 | 20.0 ± 0.00 | 20.0 ± 0.00 | 20.0 ± 0.00 | 20.0 ± 0.00 | 20.0 ± 0.00 |

TABLE 1-continued

Survival of in vitro raised shoots of mint varieties at different concentrations of menthol.

| 20 | 20 | 20.0 ± 0.00 | 20.0 ± 0.00 | 20.0 ± 0.00 | 20.0 ± 0.00 | 20.0 ± 0.00 | 20.0 ± 0.00 |
|---|---|---|---|---|---|---|---|
| 30 | 20 | 20.0 ± 0.00 | 20.0 ± 0.00 | 20.0 ± 0.00 | 20.0 ± 0.00 | 20.0 ± 0.00 | 20.0 ± 0.00 |
| 40 | 20 | 20.0 ± 0.00 | 20.0 ± 0.00 | 20.0 ± 0.00 | 20.0 ± 0.00 | 20.0 ± 0.00 | 20.0 ± 0.00 |
| 50 | 20 | 17.0 ± 0.91 | 18.0 ± 0.91 | 16.0 ± 0.90 | 19.0 ± 0.57 | 17.0 ± 0.41 | 19.4 ± 0.52 |
| 60 | 20 | 14.0 ± 0.91 | 15.0 ± 0.11 | 12.0 ± 0.71 | 16.0 ± 0.57 | 15.0 ± 0.91 | 17.0 ± 0.41 |
| 70 | 20 | 9.0 ± 0.91 | 8.0 ± 0.91 | 6.0 ± 0.32 | 10.0 ± 0.82 | 7.0 ± 0.82 | 11.0 ± 0.58 |
| 80 | 20 | 4.0 ± 0.58 | 4.0 ± 0.41 | 1.6 ± 0.31 | 5.0 ± 0.41 | 3.0 ± 0.41 | 6.0 ± 0.82 |
| 90 | 20 | 2.0 ± 0.40 | 2.0 ± 0.41 | 1.0 ± 0.41 | 3.0 ± 0.32 | 2.0 ± 0.32 | 3.0 ± 0.36 |
| 100 | 20 | 0.0 ± 0.00 | 0.4 ± 0.32 | 0.2 ± 0.26 | 0.4 ± 0.32 | 0.2 ± 0.32 | 0.4 ± 0.26 |

| Concentration of menthol | Survival after 7 days Number | | | | | |
|---|---|---|---|---|---|---|
| mg ml$^{-3}$ | Himalaya | Shivalik | Gomti | MAS-1 | Kosi | Kalka |
| 0 | 20.0 ± 0.00 | 20.0 ± 0.00 | 20.0 ± 0.00 | 20.0 ± 0.00 | 20.0 ± 0.00 | 20.0 ± 0.00 |
| 10 | 20.0 ± 0.00 | 20.0 ± 0.00 | 20.0 ± 0.00 | 20.0 ± 0.00 | 20.0 ± 0.00 | 20.0 ± 0.00 |
| 20 | 20.0 ± 0.00 | 20.0 ± 0.00 | 20.0 ± 0.00 | 20.0 ± 0.00 | 20.0 ± 0.00 | 20.0 ± 0.00 |
| 30 | 20.0 ± 0.00 | 20.0 ± 0.00 | 20.0 ± 0.00 | 20.0 ± 0.00 | 20.0 ± 0.00 | 20.0 ± 0.00 |
| 40 | 17.6 ± 0.66 | 18.0 ± 0.41 | 16.8 ± 0.48 | 18.0 ± 0.57 | 18.0 ± 0.41 | 17.6 ± 0.66 |
| 50 | 9.0 ± 0.41 | 11.0 ± 0.41 | 7.0 ± 0.41 | 13.4 ± 0.66 | 10.0 ± 0.52 | 13.8 ± 0.86 |
| 60 | 2.0 ± 0.41 | 5.0 ± 0.71 | 4.0 ± 0.57 | 10.0 ± 0.91 | 8.0 ± 0.82 | 10.0 ± 0.91 |
| 70 | 0.2 ± 0.26 | 2.0 ± 0.32 | 0.4 ± 0.32 | 3.0 ± 0.58 | 1.0 ± 0.40 | 4.0 ± 0.81 |
| 80 | 0.0 ± 0.00 | 0.0 ± 0.00 | 0.0 ± 0.00 | 0.4 ± 0.32 | 0.0 ± 0.00 | 0.0 ± 0.00 |
| 90 | 0.0 ± 0.00 | 0.0 ± 0.00 | 0.0 ± 0.00 | 0.0 ± 0.00 | 0.0 ± 0.00 | 0.0 ± 0.00 |
| 100 | 0.0 ± 0.00 | 0.0 ± 0.00 | 0.0 ± 0.00 | 0.0 ± 0.00 | 0.0 ± 0.00 | 0.0 ± 0.00 |

TABLE 2

Oil and menthol yields of varieties tested

| | Oil % | | | Menthol % | | |
|---|---|---|---|---|---|---|
| | 1$^{st}$ harvest | 2$^{nd}$ harvest | Average | 1$^{st}$ harvest | 2$^{nd}$ harvest | Average |
| Himalaya | 0.64 ± 0.06 | 0.70 ± 0.06 | 0.67 | 77.1 ± 1.4 | 78.0 ± 1.1 | 77.5 |
| Shivalik | 0.66 ± 0.09 | 0.53 ± 0.06 | 0.59 | 71.0 ± 3.8 | 8.01 ± 1.7 | 75.5 |
| Gomti | 0.65 ± 0.03 | 0.53 ± 0.03 | 0.59 | 67.6 ± 4.7 | 75.9 ± 4.2 | 71.7 |
| MAS-1 | 0.491 ± 0.06 | 0.52 ± 0.041 | 0.50 | 77.4 ± 0.5 | 83.2 ± 1.0 | 80.3 |
| Kosi | 0.74 ± 0.04 | 0.57 ± 0.13 | 0.65 | 77.7 ± 1.3 | 75.9 ± 4.2 | 76.8 |
| Kalka7 | 0.60 ± 0.00 | 0.54 ± 0.05 | 0.57 | 77.0 ± 2.1 | 82.0 ± 2.1 | 79.5 |

TABLE 3

Correlation between menthol content and survival in presence of menthol in poison agar medium

| Concentration of menthol | Correlation coefficient | |
|---|---|---|
| ($\mu$g ml$^{-1}$) | 24 h | 7 d |
| 50 | 0.838 | 0.871 |
| 60 | 0.887 | 0.646 |
| 70 | 0.891 | 0.680 |
| 80 | 0.895 | 0.542 |

Based on the survival frequencies of the tissue culture regenerated shoots of different varieties in the presence of the menthol selection pressure, the Pearson correlation coefficients were calculated using SPSS software. The survival kinetics in relation to menthol tolerance level of regenerated shoots for all the cultivars showed a definite positive co-relation with the menthol content in the essential oils of the cultivars (table 3). Thus it was obvious that the cultivars producing more amount of menthol in oil could tolerate higher amount of menthol under in vitro selection pressure meaning thereby that a definite corresponding relationship existed between the survival rate (menthol tolerance) and menthol content.

Plants are known to evolve mechanisms tither to escape or detoxify the toxic substances whether produced by it or externally supplied into the system. In this case, menthol the major monoterpene component of the essential oil, which is known to be cytotoxic to the plant higher concentrations, is expected to be produced upto a level that the cellular system can tolerate and thus limiting the yield levels. As a dependable mechanism such that the stored product could be utilized/catabolized upon need, it gets isolated in specialized tissue (trichomes). Thus it is logical to anticipate that a genotype which can tolerate higher level of menthol nay in turn be able to accumulate higher menthol by bypassing the feed back end product toxicity through the changed biochemical pathway resulting from a corresponding genetic change at DNA level. This may possibly result from genomic rearrangements leading to lifting of feedback inhibition in combination with efficient mechanisms for detoxification by excluding the toxic monoterpene to specialized tissues like trichomes. Thus the level of menthol accumulated could be linked to the tolerance levels of different cultivars. With this rationale, the possibility to generate high menthol yielding line(s) from the well adapted variety Himalaya was explored by selection of somaclones tolerant to high menthol supplied exogenously in the culture medium.-

(B) Development and application of in vitro menthol tolerance procedure for selection of menthol rich clones:

The Applicants selected the improved plant variety cv. Himalaya (U.S. Pat. PP 10,935: Kumar et al 1999) of *Mentha arvensis* L. as the base material for further improvement and selection. This variety is a hybrid between variety Gomti and Kalka and bears the high proliferating habit of Gomti and high menthol content, disease tolerant characters of Kalka. The explant material was collected from the field grown plants and surface sterilized by washing sequentially with 2% detergent, distilled water containing a few drops of Savlon (Johnson and Johnson, India), 0.1% acidified mercurie chloride and autoclaved distilled water before inoculation. About 1 cm long internode pieces were inoculated in the MS medium (Murashige and Skoog 1962) containing 0.2 $\mu$g ml$^{-1}$ concentrations of the auxin 2,4 dichlorophenoxyacetic acid (2,4-D) and 7 $\mu$g ml$^{-1}$ of the cytokinin 6-($\gamma\gamma'$-dimethylallyl amino) purine (2iP or 2aP) (Khanuja et al. 1998). This procedure has been highly efficient in generating variation in cultures of mints with greater frequencies. The cultures were grown at 25±2° C. and 400 to 600 lux light intensity with 16-h photoperiod. The regenerated shoots were separated 12 weeks latter the explant inoculation for rooting and/or screening.

The regenerated shoots (3–4 cm long, containing the apical bud and 2–3 nodes) separated from the 2,4D/2iP medium, were inoculated into MS basal medium containing vitamins, 100 mg l$^{-1}$ myo-inositol, 3% wv$^{-1}$ sucrose, 1.5% wv$^{-1}$ agar (Difco), with or without menthol (0 to 100 $\mu$g ml$^{-1}$, concentration stepped up by 10 $\mu$g serially in each treatment). On each kind of these media, 5 independent regenerated shoots were inoculated per flask; 4 flasks were inoculated per replication and each treatment was replicated 5 times, making the number of flasks to 20 and number of explants to 100 for each concentration of menthol. Like the earlier experiment this experiment was also conducted in the completely randomised design (CRD) fashion. Cultures were incubated and maintained at 25±2° C. and 400–600 lux light intensity with 16 hour photoperiod. The nature of initial responses in explants was recorded every 24 hours over a period of one week.

Browning and death of shoot tissues were observed at concentrations above 50 $\mu$g ml$^{-1}$ of menthol within 24 hours and 7 days after inoculation in case of 40 $\mu$g ml$^{-1}$ concentration. Below these concentrations, though some lower leaves completely wilted but the shoots still survived in the culture. At a concentration of 70 $\mu$g ml$^{-1}$ the shoot survival was about 45% within 24 hours of inoculation ultimately leading to death of majority of shoots (almost 99%) within 7days after inoculation. No shoots were able to survive at and above 80 $\mu$g ml$^{-1}$ menthol after 7th day (Table 4). Therefore, the concentration 70 $\mu$g ml$^{-1}$ menthol was taken as the concentration for large scale screening of the tolerant clone(s) to be selected.

Large scale screening of clones was carried out in various batches by raising the calliclones as above. A total of 2850 shoots were transferred to the screening medium containing 50 $\mu$g ml$^{-1}$ menthol and incubated for 1 week. The surviving shoots from this medium were stepwise transferred to media containing higher concentrations of menthol (60 and 70 g ml$^{-1}$). Finally the tolerant clones surviving at 70 $\mu$g ml$^{-1}$ menthol concentration were transferred individually to MS basal medium containing vitamins for rooting. The looted plantlets were subsequently hardened and transferred to pots in the glass house to raise sufficient planting material (sucker) for field experiments.

After 7 days of culture 1263 twigs survived at 50 $\mu$g ml$^{-1}$ concentration of menthol. These surviving shoots were subsequently transferred to the medium containing 60 $\mu$g ml$^{-1}$ menthol At this concentration 942 twig turned brown and died within 7 days. Finally, the 321 twigs which survived were inoculated into the screening medium containing 70 $\mu$g ml$^{-1}$ menthol. In His tertiary level screening, only 30 shoots survived (Table 5). These clones were inoculated into the rooting medium and after rooting transferred to pots in the glasshouse. The acclimatized selected plantlets from the glasshouse were transferred to the field for sucker production in the month of September 1997. In the month of January 1998, the suckers developed from each plant were field planted with 5 replicates using randomized block design. The plants grown with standard agronomic practices were harvested twice, first after 110 days of planting and subsequently 70 days after the first harvest. Ultimately, these 30 menthol tolerant clones were multiplied and grown in the field in replicated plots of 5 m×5 m sizes. The twigs of 30 clones from the replicated trials were rechecked for tolerant phenotypes at a concentration of 70 $\mu$g ml$^{-1}$ menthol wherein, these survived even after 7 days. These were also tested for survival at one step higher concentration of menthol (80 $\mu$g ml$^{-1}$). At this concentration of menthol only 5 clones (GRB 3, 14, 24, 27, 30) survived.

Plant shoot samples (500 g) collected from each treatment in the replicated trials wire subjected to hydrodistillation for extraction of the essential oil to determine the oil yield of the selected clones. The oil samples were subjected to GLC analysis for estimating the menthol content (oil quality). Menthol yield per g shoot biomass was also estimated for comparative menthol productivity of these genotypes (Table 6). While 6 of these clones (GRB 6, 24, 26, 27, 29 and 30) yielded about 1% oil in the first harvest, three clones namely GRB 24, 27 and 30 produced about 2% oil in the second harvest. Comparison for menthol yield per unit shoot showed that majority of the selected clones produced more amount of total menthol per gram biomass in the two harvests than the control cv. Himalaya. Superiority of menthol production per gram shoot mass was highly significant in clones GRB 24, 27 and 30 (23.04, 24.91 and 25.05 mg per g shoot mass respectively) compared to 10.58 mg g$^{-1}$ by the control cv. Himalaya.

To mark the genetic variations at molecular level and confirming uniformity in the menthol tolerant clones, DNA was isolated from leaf tissue according to the protocol developed in the laboratory (S P S Khanuja, A K Shasany, M P Darokar and S Kumar, 1999, Rapid isolation of DNA from dry and fresh samples of plants producing large amounts of secondary metabolites and essential oils. Plant Molecular Biology Reporter 17: 74 and electronic article location: http://www.chemweb.com/library/kluwer/pmbrdisplay.exe?jcode=pmbr). Polymerase chain reactions (PCRs) were carried out in 25 $\mu$l volume. A reaction tube contained 25 ng of DNA, 0.2 unit of Taq DNA polymerase, 100 $\mu$M each of dNTPs, 1.5 mM MgCl$_2$ and 5 p mol of decanucleotide primers. The amplifications were carried out using the DNA Engine thermal cycler (MJ Research, USA) providing conditions defined in the above procedure. The amplified products were loaded in 1.2% agarose gel containing 0.5 $\mu$g ml$^{-1}$ of ethidium bromide and photographed by Polaroid system. Fourty decamer primers procured from Operon Technologies, USA (OPJ and OPT) were used to detect polymorphism in the selected clones.

Figure 1A:
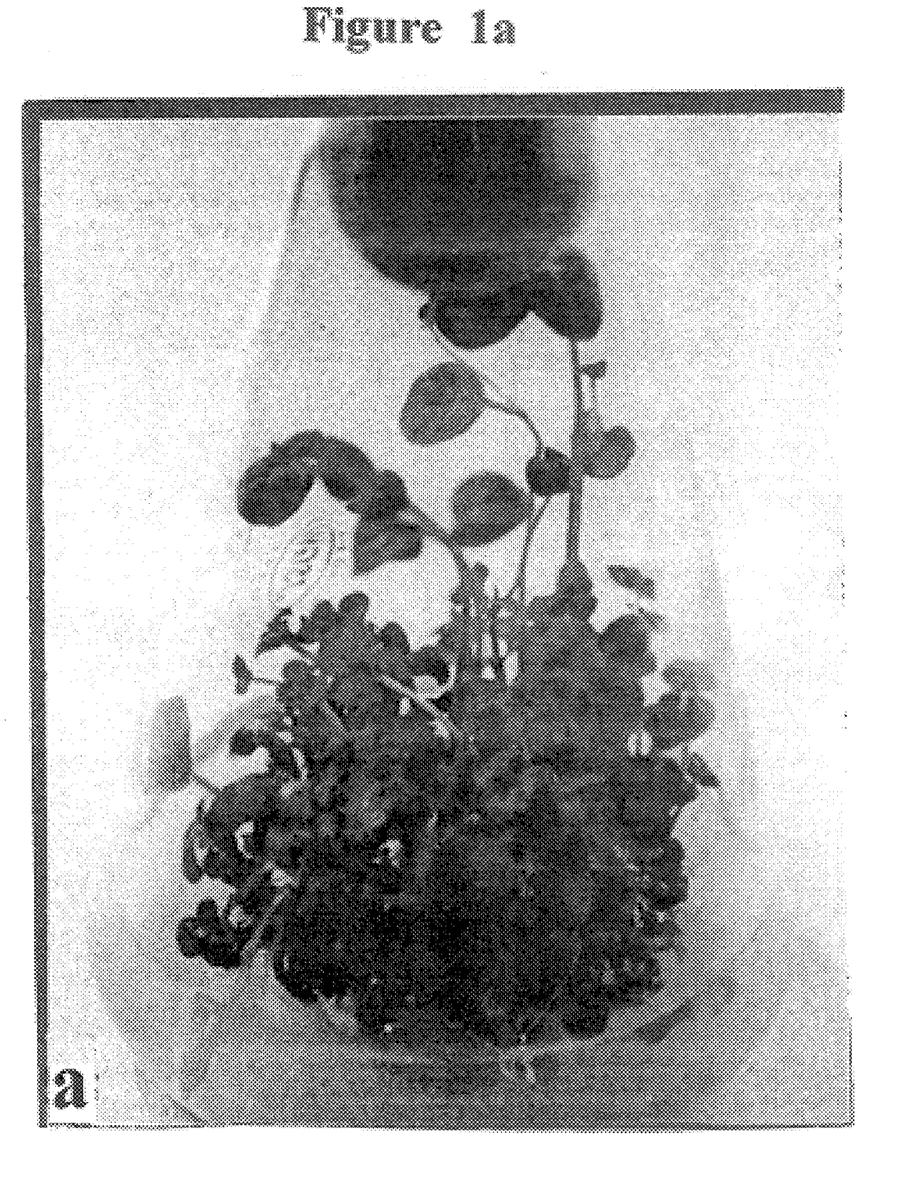
FIG. 1a: represents regenerated shoots (calliclones)12 weeks after the internodal explant inoculation in 0.2 $\mu g$ ml$^{-1}$ 2,4-D and 7 $\mu g$ ml$^{-1}$ 2iP.
Figure 1B:
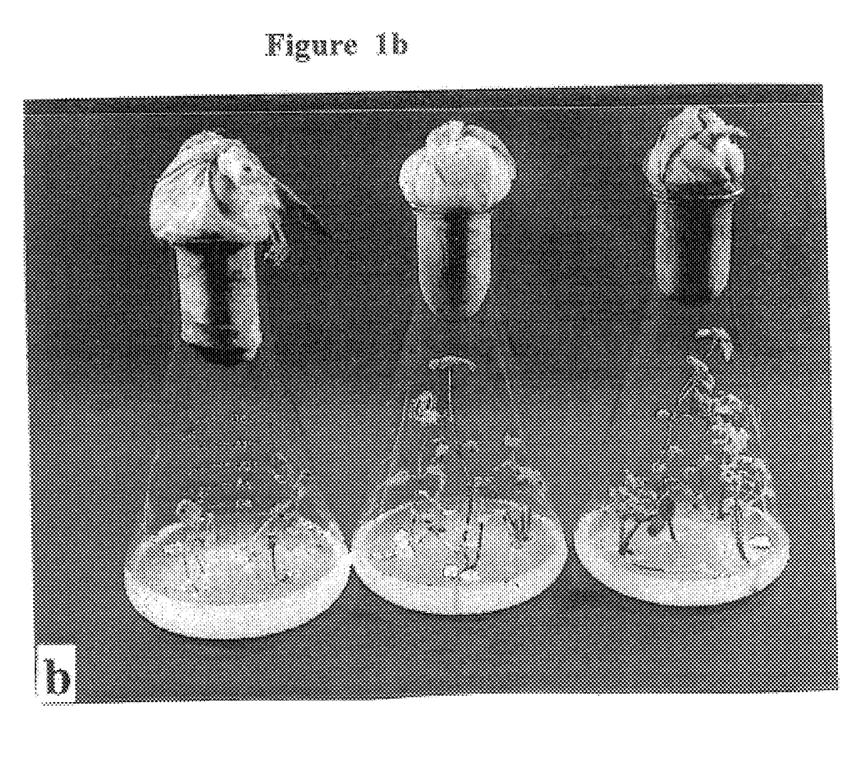
FIG. 1b: represents shoots inoculated in the medium containing menthol (Left flask is control showing browning and death after 24 hours)
Figure 1C:
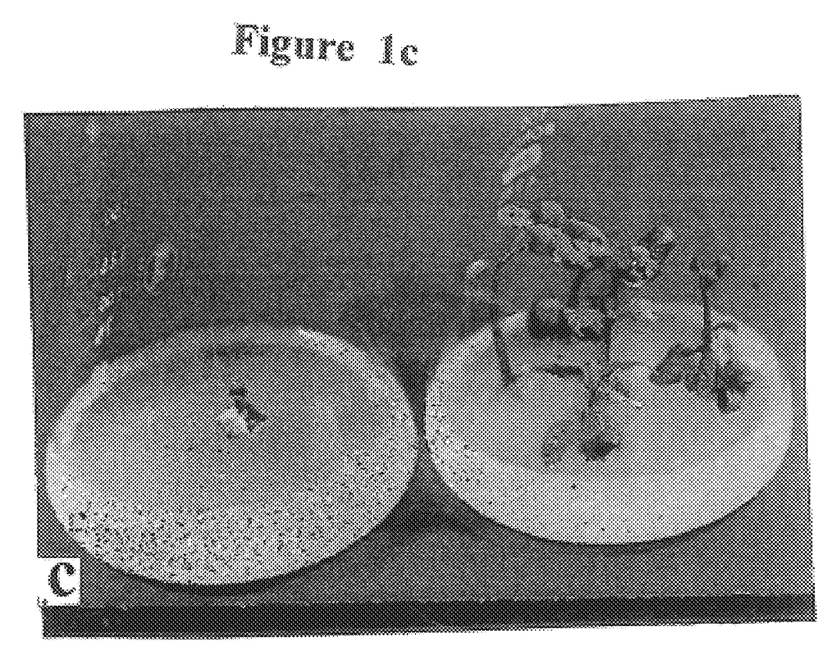
FIG. 1c: represents selected five clones growing in menthol (80 $\mu g$ ml$^{-1}$) containing medium, after 7 days(Left flask is control).
Figure 1D:
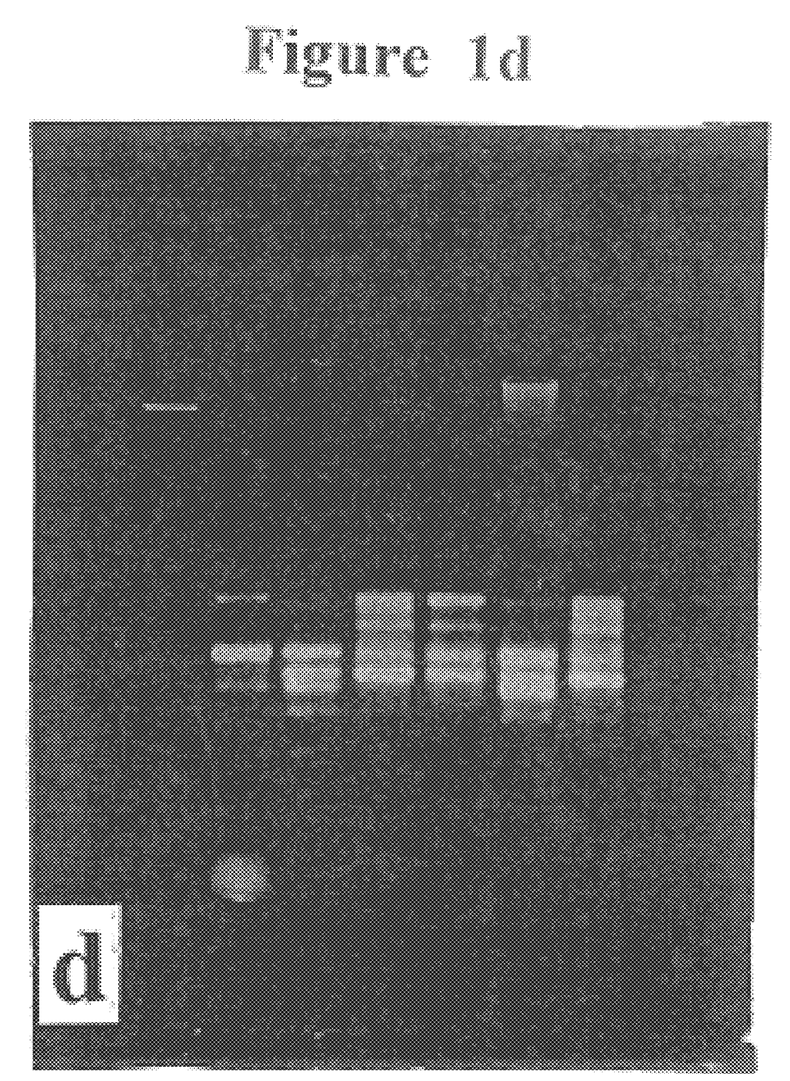
FIG. 1d: represents RAPD profiles of five selected clones with OPT 04 showing differentiation among genotypes and the control.
Figure 1E:
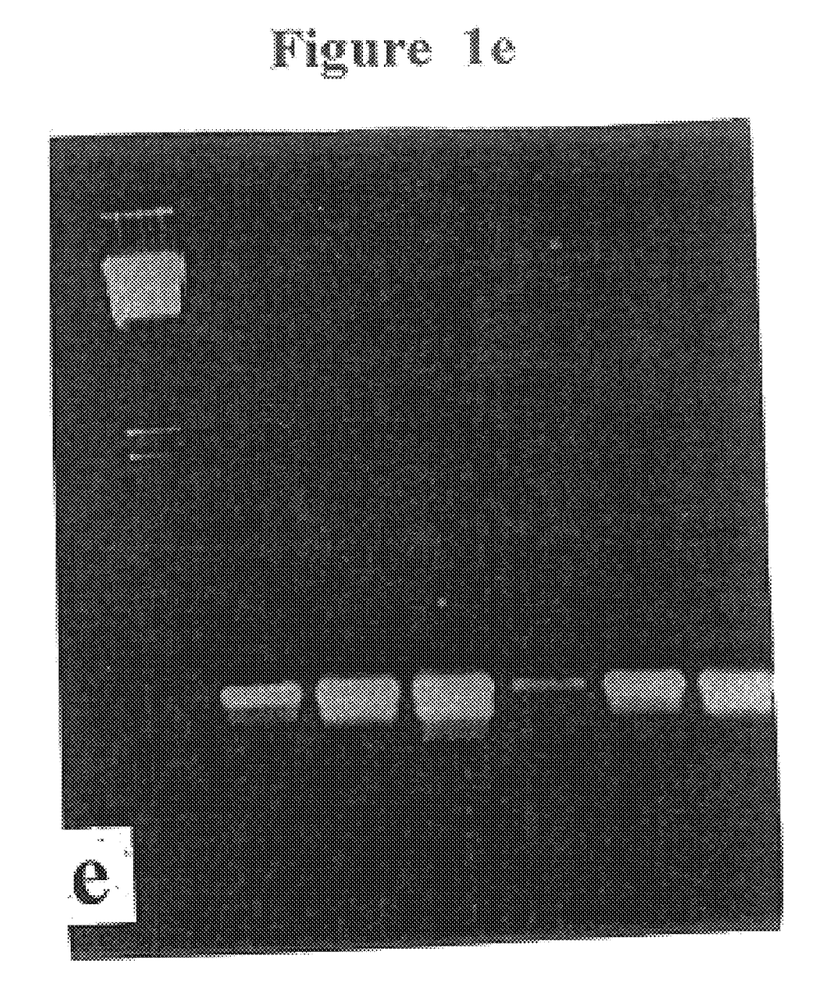
FIG. 1e: represents RAPD profiles of five selected clones with OPT 05 showing differentiation among genotypes and with control.

Among the variants selected for higher tolerance level against menthol, five clones (GRB 3, 14 24, 27 and 30) were found to be consistent in their phenotypes surviving even under 80 $\mu$g ml$^{-1}$ menthol. Since these were the result of independent selection experiments, the variation at molecular level was assessed tough RAPD analysis to compare them with parent cv. Himalaya as well as among themselves. Polymorphic bands differentiating these genotypes could be detected using 40 random primers establishing their distinctiveness (FIG. 1, Table 7) After multiplying these clones through high efficiency micropropagation protocol (Shasany et al 1998), randomly 100 clones from each genotype was tested for polymorphism with 40 random primers. No RAPD variation was observed in established clones indicating uniformity and genetic stability of the selected clones.

TABLE 4

Survival of callus mediated regenerants from internodal explants at different concentrations of menthol.

| Concentration of menthol ($\mu g\ ml^{-1}$) | Number of shoots tested per replication* | Survival after 24 hours Number | % | Survival after 7 days Number | % |
|---|---|---|---|---|---|
| 0 | 20 | 20.0 ± 0.00 | 100 | 20.0 ± 0.00 | 100 |
| 10 | 20 | 20.0 ± 0.00 | 100 | 20.0 ± 0.00 | 100 |
| 20 | 20 | 20.0 ± 0.00 | 100 | 20.0 ± 0.00 | 100 |
| 30 | 20 | 20.0 ± 0.00 | 100 | 20.0 ± 0.00 | 100 |
| 40 | 20 | 20.0 ± 0.00 | 100 | 17.6 ± 0.66 | 88 |
| 50 | 20 | 17.0 ± 0.91 | 85 | 9.0 ± 0.41 | 45 |
| 60 | 20 | 14.0 ± 0.58 | 70 | 2.0 ± 0.41 | 10 |
| 70 | 20 | 9.0 ± 0.91 | 45 | 0.2 ± 0.26 | 1 |
| 80 | 20 | 4.0 ± 0.58 | 20 | 0.0 ± 0.00 | 0 |
| 90 | 20 | 2.0 ± 0.40 | 10 | 0.0 ± 0.00 | 0 |
| 100 | 20 | 0.0 ± 0.00 | 0 | 0.0 ± 0.00 | 0 |

*Each replication consisted of 4 flasks each containing 5 shoots and 5 replicates of each treatment were included in the experiment

TABLE 5

Large scale screening and survival of regenerated clones at different concentrations of menthol

| Screening for menthol tolerance | Shoots screened | Survival in medium containing menthol ($\mu g\ ml^{-1}$) 50 | 60 | 70 |
|---|---|---|---|---|
| Number | 2850 | 1263 | 321 | 30 |
| Percentage | 100 | 44.31 | 11.26 | 1.05 |

TABLE 6

Comparative oil and menthol yields of the menthol tolerant clones in field evaluation.

| Clone | Oil yield (%) First harvest | Second harvest | Menthol content of oil (%) First harvest | Second harvest | Menthol yield (mg per g biomass) First harvest | Second harvest | Total |
|---|---|---|---|---|---|---|---|
| GRB1. | 0.81 ± 0.07 | 1.17 ± 0.12 | 69.9 ± 5.0 | 80.1 ± 1.8 | 5.87 ± 0.83 | 9.33 ± 0.94 | 15.2 ± 1.77 |
| GRB2. | 0.81 ± 0.13 | 1.00 ± 0.15 | 75.1 ± 2.5 | 79.2 ± 1.4 | 6.11 ± 1.09 | 7.92 ± 1.31 | 14.03 ± 2.4 |
| GRB3. | 0.88 ± 0.06 | 1.45 ± 0.09 | 76.1 ± 1.4 | 80.3 ± 0.4 | 6.71 ± 0.33 | 11.68 ± 0.72 | 18.39 ± 1.05 |
| GRB4. | 0.79 ± 0.57 | 0.77 ± 0.09 | 77.7 ± 2.2 | 83.0 ± 2.2 | 6.09 ± 0.13 | 6.35 ± 0.59 | 12.44 ± 0.72 |
| GRB5. | 0.84 ± 0.03 | 1.30 ± 0.10 | 77.6 ± 1.3 | 79.6 ± 1.5 | 6.55 ± 0.15 | 10.33 ± 0.90 | 16.88 ± 1.05 |
| GRB6. | 0.93 ± 0.08 | 1.06 ± 0.09 | 76.9 ± 2.8 | 81.6 ± 0.8 | 7.15 ± 0.44 | 8.67 ± 0.79 | 15.82 ± 1.23 |
| GRB7. | 0.80 ± 0.06 | 1.36 ± 0.07 | 76.8 ± 1.3 | 78.0 ± 1.4 | 6.16 ± 0.53 | 10.62 ± 0.72 | 16.78 ± 1.25 |
| GRB8. | 0.85 ± 0.12 | 1.18 ± 0.14 | 75.6 ± 0.6 | 78.4 ± 0.7 | 6.44 ± 0.99 | 9.24 ± 0.69 | 15.68 ± 1.68 |
| GRB9. | 0.85 ± 0.03 | 1.40 ± 0.15 | 75.0 ± 1.3 | 76.5 ± 2.2 | 6.38 ± 0.27 | 10.75 ± 1.15 | 17.13 ± 1.42 |
| GRB10. | 0.53 ± 0.02 | 0.90 ± 0.10 | 75.1 ± 1.1 | 76.0 ± 1.7 | 4.00 ± 0.12 | 6.88 ± 0.89 | 10.88 ± 1.01 |
| GRB11. | 0.72 ± 0.07 | 1.19 ± 0.28 | 74.6 ± 0.8 | 78.8 ± 0.9 | 5.42 ± 0.55 | 9.44 ± 2.31 | 14.86 ± 2.86 |
| GRB12. | 0.69 ± 0.05 | 1.08 ± 0.25 | 74.8 ± 2.3 | 75.6 ± 2.3 | 5.17 ± 0.47 | 8.11 ± 1.77 | 13.28 ± 2.24 |
| GRB13. | 0.71 ± 0.08 | 1.04 ± 0.12 | 70.5 ± 3.2 | 71.9 ± 0.3 | 5.20 ± 0.67 | 7.67 ± 0.94 | 12.87 ± 0.61 |
| GRB14. | 0.70 ± 0.03 | 1.45 ± 0.36 | 73.4 ± 1.3 | 77.8 ± 0.8 | 5.38 ± 0.21 | 11.33 ± 2.86 | 16.71 ± 3.07 |
| GRB15. | 0.65 ± 0.12 | 1.28 ± 0.43 | 75.4 ± 0.4 | 79.1 ± 0.7 | 5.79 ± 1.02 | 10.14 ± 3.50 | 15.93 ± 4.52 |
| GRB16. | 0.82 ± 0.05 | 0.59 ± 0.15 | 76.3 ± 0.9 | 74.3 ± 0.3 | 6.86 ± 0.52 | 4.40 ± 1.10 | 11.26 ± 1.62 |
| GRB17. | 0.58 ± 0.07 | 1.12 ± 0.32 | 77.5 ± 0.9 | 77.9 ± 1.3 | 5.16 ± 0.20 | 8.69 ± 2.45 | 13.85 ± 2.65 |
| GRB18. | 0.73 ± 0.04 | 1.02 ± 0.27 | 79.3 ± 0.9 | 77.6 ± 2.3 | 6.05 ± 0.26 | 7.89 ± 2.02 | 13.94 ± 2.28 |
| GRB19. | 0.75 ± 0.06 | 1.49 ± 0.17 | 75.6 ± 1.8 | 79.6 ± 1.3 | 5.93 ± 0.34 | 11.91 ± 1.55 | 17.84 ± 1.89 |
| GRB20. | 0.77 ± 0.04 | 0.72 ± 0.20 | 76.8 ± 0.1 | 71.1 ± 4.1 | 5.63 ± 0.13 | 4.99 ± 1.17 | 10.62 ± 1.30 |
| GRB21. | 0.75 ± 0.03 | 1.40 ± 0.34 | 74.2 ± 0.7 | 80.8 ± 1.7 | 5.69 ± 0.29 | 11.38 ± 2.85 | 17.07 ± 3.14 |
| GRB22. | 0.88 ± 0.06 | 0.99 ± 0.33 | 74.1 ± 1.2 | 72.6 ± 8.2 | 5.98 ± 0.18 | 7.39 ± 1.60 | 13.37 ± 1.78 |
| GRB23. | 0.78 ± 0.06 | 0.86 ± 0.17 | 75.6 ± 1.2 | 75.6 ± 3.3 | 6.32 ± 0.59 | 6.43 ± 1.02 | 12.75 ± 1.61 |
| GRB24. | 1.03 ± 0.09 | 1.91 ± 0.38 | 76.7 ± 1.3 | 76.2 ± 1.6 | 8.60 ± 0.73 | 14.44 ± 2.63 | 23.04 ± 3.36 |
| GRB25. | 0.84 ± 0.02 | 0.96 ± 0.02 | 73.9 ± 0.4 | 83.6 ± 0.9 | 6.09 ± 0.19 | 7.74 ± 0.18 | 13.83 ± 0.37 |
| GRB26. | 1.14 ± 0.20 | 1.36 ± 0.41 | 74.0 ± 0.5 | 77.7 ± 2.5 | 6.91 ± 0.17 | 10.66 ± 3.49 | 17.57 ± 3.66 |
| GRB27. | 1.06 ± 0.05 | 2.03 ± 0.52 | 74.5 ± 0.5 | 80.9 ± 1.9 | 8.24 ± 0.11 | 16.67 ± 4.55 | 24.91 ± 4.66 |
| GRB28. | 0.85 ± 0.06 | 0.88 ± 0.11 | 76.0 ± 0.2 | 79.1 ± 0.8 | 6.96 ± 0.23 | 6.98 ± 0.78 | 13.94 ± 1.01 |
| GRB29. | 0.94 ± 0.04 | 0.87 ± 0.03 | 64.7 ± 7.7 | 80.6 ± 1.4 | 6.13 ± 0.63 | 7.05 ± 0.30 | 13.18 ± 0.93 |
| GRB30. | 0.95 ± 0.03 | 2.22 ± 0.60 | 77.7 ± 1.0 | 80.7 ± 1.4 | 7.12 ± 0.06 | 17.93 ± 0.45 | 25.05 ± 0.51 |
| Control Himalaya | 0.64 ± 0.06 | 0.70 ± 0.06 | 77.1 ± 1.4 | 78.0 ± 1.1 | 5.12 ± 0.22 | 5.46 ± 0.45 | 10.58 ± 0.67 |

TABLE 7

Polymorphic bands observed in the RAPD profiles of the clones with different primers compared to cv. Himalaya.

| Clones | Primers showing polymorphic bands |
| --- | --- |
| GRB 3 | OPJ 09, 17 and OPT 04, 05, 12, 20 |
| GRB 14 | OPJ 05, 14, 15, 16, 17 and OPT 04, 05, 13, 15, 16 |
| GRB 24 | OPT 05, 08 |
| GRB 27 | OPJ 08 and OPT 04, 13, 17 |
| GRB 30 | OPJ 01, 03, 09, 16, 19, 20 and OPT 01, 04, 05, 08, 12, 16, 20 |

The menthol rich clones selected through this procedure were having the following morphological characteristics observed during 110–120 days after planting (Examples GRB 27 and 30).

| | | |
| --- | --- | --- |
| 1. Plant height: | At least 72.0 to 74.0 cm | |
| 2. Leaf: | | |
| Colour | Green(138 A–B) | |
| Length | 8.0 to 8.6 cm | |
| Width | 5.2 to 5.6 cm | |
| Area | 15.6 to 15.8 cm | |
| Petiole length | 2.0 to 2.2 cm | |
| 3. Leaf: stem ratio (w/w) | At least 1.2 to 1.5 | |
| 4. Inflorescence | Indefinite recemose | |
| | Total number of florets 20 to 35 | |
| 5. Flowers | | |
| Arranged in whorls surrounding the stem at the base of lateral leaves. | | |
| Calyx | Four, Green (143 C) | |
| Corolla | Pinkish white (56 C–D), four, fused to a bell shaped corolla tube | |
| Anthers | Four, ocidimetary | |
| Stigma | Bifid, white | |
| 6. Oil content in the fresh herb (%): | At least 0.90 to 1.10 (Harvest after 110 days) | |
| 7. Oil quality: | | |
| Menthol content (%) | At least 74% | |
| Congealing point | 2 to 21° C. | |

Protocol to Screen Menthol Tolerant Plants

Step A: Explant, Culture Conditions and Regeneration for Generating Genetically Modified Somaclones 1. The *Mentha arvensis* cv Himalaya explant material was collected from the field grown plants and washed sequentially with 2% detergent, distilled water containing a few drops of Savlon (Johnson and Johnson, India), 0.1% acidified mercuric chloride and autoclaved distilled water. About 1 cm long internode pieces were inoculated in the MS media (Murashige T, Skoog F. 1962. A revised medium for rapid growth and bioassay with tobacco tissue cultures. *Physiol. Planta.* 15:473–497.) containing the auxin, 0.2 $\mu g\ ml^{-1}$ 2,4 dichlorophenoxy acetic acid (2,4-D) and the cytokinin, 7 $\mu g\ ml^{-1}$ 6-(γγ'-dimethylallyl amino) purine (2iP or 2aP). Explants can also be inoculated in any other medium with suitable auxin and cytokinin ratio favouring callus leading to regeneration.
2. The cultures were grown at 25±2° C. and 400 to 600 lux light intensity with 16 h photoperiod.
3. The regenerated shoots were separated at 12 weeks from the explant inoculation and transferred to the MS medium free of hormones for rooting.
4. Alternatively a large population of independent clones can be raised either through callus mediated regeneration or other in vitro methods permitting appearance of somaclonal variation or through vegetative propagation means.
5. The plantlets thus generated were examined for any genotypic change by comparing their RAPD profiles with that of cv Himalaya using the 12 random decanucleotide primers having the sequences AAATCGGAGC (SEQ ID NO 1), GTCCTACTCG (SEQ ID NO 2), GTCCTTAGCG (SEQ ID NO 3), TGCGCGATCG (SEQ ID NO 4), AACGTACGCG (SEQ ID NO 5), GCACGCCGGA (SEQ ID NO 6), CACCCTGCGC (SEQ ID NO 7), CTATCGCCGC (SEQ ID NO 8), CGGGATCCGC (SEQ ID NO 9), GCGAATTCCG (SEQ ID NO 10), CCCTGCAGGC (SEQ ID NO 11), CCAAGCTTGC (SEQ ID NO 12).

In this invention, the Applicants accumulated a large number of molecular variants after screening which were different from 'Himalaya' with one or more primer, out of the 12 primer used.

Step B: Screening these Genetically Modified Clones for Menthol Tolerance

1. The regenerated shoots/plantlets were then inoculated in the MS basal medium in replicates in presence of toxic concentrations of menthol along with the control parental clone.
2. Large scale screening of the heterogeneous population of molecular variants were carried out by inoculating the regenerated independent clones into the screening medium i.e., MS basal agar containing 50 $\mu g\ ml^{-1}$ menthol followed by incubation for 1 week.
3. The surviving shoots from this medium were step-wise transferred to media containing higher concentrations of menthol (60 and 70 $\mu g\ ml^{-1}$). Finally the tolerant clones surviving at 70 $\mu g\ ml^{-1}$ menthol concentration (which cause 99% killing) are transferred individually to MS basal medium containing vitamins for rooting.
4. The individual molecular variants selected through menthol screening of regenerated clones were multiplied from the internode segments, which were inoculated in MS based media containing vitamins, 100 $\mu g\ ml^{-1}$ myo-inositol, 3% $wv^{-1}$ sucrose, 1.5% $wv^{-1}$ agar (Difco), 0.5 $\mu g\ ml^{-1}$ NAA (1-napthalene acetic acid) and 5 $\mu g\ ml^{-1}$ BAP (6benzyl aminopurine)
5. The cultures were grown at 25±2° C. and 400 to 600 lux light intensity with 16 h photoperiod.
6. These clones were tested for uniformity through RAPD profiling after isolating DNA from 40 mg of tissue, using the random primers (AAATCGGAGC (SEQ ID NO 1), GTCCTACTCG (SEQ ID NO 2), GTCCTTAGCG (SEQ ID NO 3), TGCGCGATCG (SEQ ID NO 4), AACGTACGCG (SEQ ID NO 5), GCACGCCGGA (SEQ ID NO 6), CACCCTGCGC (SEQ ID NO 7), CTATCGCCGC (SEQ ID NO 8), CGGGATCCGC (SEQ ID NO 9), GCGAATTCCG (SEQ ID NO 10), CCCTGCAGGC (SEQ ID NO 11), CCAAGCTTGC (SEQ ID NO 12)). The clones were found to be similar in their profiles in comparison to the parental genetically distinct somaclones but were distinctly different from the Plant 'Himalaya'.
7. These regenerated shoots were grown in MS medium without growth hormones for rooting for 12 weeks.
8. The rooted plantlets were subsequently hardened and transferred to pots in the glass house to raise sufficient planting material (sucker) for field experiments.
9. The tolerant plants growing in the field were again brought to tissue culture for checking the menthol tolerance level at the critical concentration (70 $\mu g\ ml^{-1}$) and at higher level (80$\mu g\ ml^{-1}$)
10. The plant shoot material was collected from each tolerant clone, oil is hydro-distilled and menthol content of the essential oil is analyzed through GLC.

11. Those clones, which showed the stability of menthol tolerance, were selected, multiplied and analyzed for genetic uniformity and distinctiveness at DNA level among the multiplied propagules through RAPD analysis.

What is claimed is:

1. A rapid in vitro method for selection of menthol rich mint genotypes from large population of independent clones, said method comprising the steps of:
   (i) raising a heterogeneous population of *Mentha arvensis* clones in vitro or by vegetative methods,
   (ii) transferring the plantlets/shoots to a basal medium containing selective compounds in an amount sufficient to cause toxic effect in more than 95% of the clones,
   (iii) selecting surviving clones, their hardening in the glasshouse, transfer to field, reconfirmation of menthol tolerance through repeated in vitro assays, and
   (iv) multiplying selected clones and confirming genetic uniformity through RAPD analysis before menthol yield field trial.

2. A method as claimed in claim 1, wherein the menthol rich mint genotypes yield at least 74% or more menthol in their essential oils.

3. A method as claimed in claim 1, wherein the said screening method is used as a rapid indicator of menthol yield in different varieties for evaluation purpose.

4. A method as claimed in claim 1, wherein the said selection pressure is the concentration of menthol from about 50 to about 80 $\mu g\ ml^{-1}$, causing lethality of more than 95% of clones.

5. A method as claimed in claim 1 wherein the most preferred compounds for selection present in the basal medium include monoterpenes and menthol.

6. A method as claimed in claim 1, wherein the said compounds for selection are toxic to cytoplasm causing complete loss of chlorophyll in the lower leaves and gradually covering the whole shoot within a week time leading to death of the shoot.

7. A method as claimed in claim 1, wherein the compounds for selection are selected from the group comprising nerol geraniol, citronellol, linalool, myrcene, terpineol, limolene, cineole, terpinol, terpinene, cymene, thymol, carvone, pinene, fenchol, fenchone, camphene, borneol, camphor, thujone, thujanol, sabinene, carene and other related compounds.

8. A method as claimed in claim 1, wherein the said procedure can be carried out in any suitable agar medium with selective compound in sterilizable flasks, tubes or containers of various sizes permitting the proper growth conditions to the shoots/plantlets.

* * * * *

```
                          SEQUENCE LISTING

<160> NUMBER OF SEQ ID NOS: 12

<210> SEQ ID NO 1
<211> LENGTH: 10
<212> TYPE: DNA
<213> ORGANISM: Mentha arvensis

<400> SEQUENCE: 1
aaatcggagc                                                          10

<210> SEQ ID NO 2
<211> LENGTH: 10
<212> TYPE: DNA
<213> ORGANISM: Mentha arvensis

<400> SEQUENCE: 2
gtcctactcg                                                          10

<210> SEQ ID NO 3
<211> LENGTH: 10
<212> TYPE: DNA
<213> ORGANISM: Mentha arvensis

<400> SEQUENCE: 3
gtccttagcg                                                          10

<210> SEQ ID NO 4
<211> LENGTH: 10
<212> TYPE: DNA
<213> ORGANISM: Mentha arvensis

<400> SEQUENCE: 4
tgcgcgatcg                                                          10

<210> SEQ ID NO 5
<211> LENGTH: 10
<212> TYPE: DNA
<213> ORGANISM: Mentha arvensis

<400> SEQUENCE: 5
aacgtacgcg                                                          10

<210> SEQ ID NO 6
<211> LENGTH: 10
<212> TYPE: DNA
<213> ORGANISM: Mentha arvensis

<400> SEQUENCE: 6
gcacgccgga                                                          10

<210> SEQ ID NO 7
<211> LENGTH: 10
<212> TYPE: DNA
<213> ORGANISM: Mentha arvensis

<400> SEQUENCE: 7
caccctgcgc                                                          10
```

```
<210> SEQ ID NO 8
<211> LENGTH: 10
<212> TYPE: DNA
<213> ORGANISM: Mentha arvensis

<400> SEQUENCE: 8
ctatcgccgc                                                               10

<210> SEQ ID NO 9
<211> LENGTH: 10
<212> TYPE: DNA
<213> ORGANISM: Mentha arvensis

<400> SEQUENCE: 9
cgggatccgc                                                               10

<210> SEQ ID NO 10
<211> LENGTH: 10
<212> TYPE: DNA
<213> ORGANISM: Mentha arvensis

<400> SEQUENCE: 10
gcgaattccg                                                               10

<210> SEQ ID NO 11
<211> LENGTH: 10
<212> TYPE: DNA
<213> ORGANISM: Mentha arvensis

<400> SEQUENCE: 11
ccctgcaggc                                                               10

<210> SEQ ID NO 12
<211> LENGTH: 10
<212> TYPE: DNA
<213> ORGANISM: Mentha arvensis

<400> SEQUENCE: 12
ccaagcttgc                                                               10
```